US006622568B2

(12) United States Patent
Nelson et al.

(10) Patent No.: US 6,622,568 B2
(45) Date of Patent: Sep. 23, 2003

(54) NON-DESTRUCTIVE STRENGTH MEASUREMENT BY PROMPT BULK HEATING METHOD

(75) Inventors: James M. Nelson, Sumner, WA (US); Richard H. Bossi, Renton, WA (US); John E. Shrader, Mercer Island, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 09/811,952

(22) Filed: Mar. 19, 2001

(65) Prior Publication Data

US 2002/0129659 A1 Sep. 19, 2002

(51) Int. Cl.$^7$ .................................................. G01L 1/24
(52) U.S. Cl. ............................................................ 73/800
(58) Field of Search .............................. 356/301, 502, 356/35.5; 372/92; 73/766, 800, 801, 802

(56) References Cited

U.S. PATENT DOCUMENTS

| | | | | |
|---|---|---|---|---|
| 4,367,961 A | * | 1/1983 | Griffin | 374/46 |
| 5,170,666 A | * | 12/1992 | Larsen | 73/571 |
| 5,361,641 A | * | 11/1994 | Eldridge et al. | 73/842 |
| 5,437,193 A | * | 8/1995 | Schleitweiler et al. | 73/830 |
| 5,438,402 A | * | 8/1995 | Gupta | 356/35.5 |
| 5,587,532 A | * | 12/1996 | Rose | 73/571 |
| 5,641,912 A | * | 6/1997 | Manahan, Sr. | 374/50 |
| 5,682,236 A | * | 10/1997 | Trolinger et al. | 356/345 |

OTHER PUBLICATIONS

Wright et al., "Particle Bonding, Annealing Response, and Mechanical Properties of Dynamically Consolidated Type 304 Stainless Steel Powders", 20A Metallurgial Transactions, Nov. 1989, 2449–2457.

Novikov et al., "Stress Wave Propagation and Fracture Processes in Metals During Rapid Bulk Heating", 26 Strength of Materials, 1994, 137–140.

Veidt et al., "Ultrasonic Evaluation of Thin, Fiber–Reinforced Laminates", 28 J. of Composite Materials, 1994, 329–342.

Kolgatin et al., "Spall Damage to a Liquid Metal Accompanying Pulsed Action of Radiation", Plenum Publishing Corporation, 1985, 702–707.

R.M. White, "Generation of Elastic Waves by Transient Surface Heating", 34 J. of Applied Physics, Dec. 1963, 3559–3567.

Tret'yachenko et al., "Thermal Deformation and Strength of Composite Materials at High Temperatures", Plenum Publishing Corporation, 1987, 545–550.

* cited by examiner

Primary Examiner—Max Noori
(74) Attorney, Agent, or Firm—Harness Dickey & Pierce P.L.C.

(57) ABSTRACT

A method and system for measuring a strength of a test specimen are provided. The method includes the steps of selecting a tensile load of interest for the test specimen, and bulk heating the test specimen at a localized region such that the test specimen is placed under the tensile load of interest. The method further provides for determining whether the tensile load of interest has caused a failure at the localized region. Bulk heating the test specimen provides a nondestructive evaluation technique that is unachievable through conventional approaches.

19 Claims, 10 Drawing Sheets

NON-DESTRUCTIVE STRENGTH MEASUREMENT BY PROMPT BULK HEATING METHOD

BACKGROUND OF THE INVENTION

1. Technical Field

The present invention relates generally to the strength measurement of composite materials. More particularly, the invention relates to a non-destructive method and system for measuring a minimum strength of a test specimen that involves bulk heating the test specimen at a localized region.

2. Discussion

In the aircraft design industry, a number of complex parameters such as aerodynamics, weight, and structural load resistance must all be considered and delicately balanced with various cost considerations. Structural load resistance (or strength) can be a particularly difficult parameter to work with at the design phase. For example, a typical aircraft will have hundreds of bonded composite materials, each having distinct strength requirements based on the anticipated load to be applied to the aircraft at the given location.

Conventional strength measurement approaches involve proof testing an entire structure, where the entire structure includes several substructures of interest. For example, the structure might be an entire aircraft wing made up of various stringers and ribs bonded to an outer skin. Although the substructure of interest may be only the outboard leading edge of the wing, conventional proof testing requires a loading fixture large enough to test the entire aircraft wing. It is easy to understand that such an approach can be quite costly, time consuming and inefficient. It is therefore desirable to provide a method for measuring a strength of a test specimen at a localized region.

SUMMARY OF THE INVENTION

The above and other objectives are provided by a method for measuring a strength of a test specimen in accordance with the present invention. The method includes the steps of selecting a tensile load of interest for the test specimen, and bulk heating the test specimen at a localized region such that the test specimen is placed under the tensile load of interest. The method further provides for determining whether the tensile load of interest has caused a failure at the localized region. Bulk heating the test specimen provides a non-destructive evaluation (NDE) technique that is unachievable through conventional approaches.

Further in accordance with the present invention, a method for determining whether a tensile load of interest has caused a failure at a localized region of a test specimen. The method provides for observing a free surface of the test specimen with an optical interferometer. A measurement response of the free surface is determined with the optical interferometer, where the measurement response results from the tensile load of interest. The method further provides for determining whether the measurement response corresponds to a failure of the test specimen. In a highly preferred embodiment, surface velocity is selected as the measurement response.

In another aspect of the invention, a strength measurement system is provided. The strength measurement system includes a test cell, an electron accelerator, and a surface measurement system. The test cell contains a test specimen, and the electron accelerator applies electron beam irradiation to the test specimen. The electron beam irradiation bulk heats the test specimen at a localized region such that the test specimen is placed under a tensile load of interest. The surface measurement system determines whether the tensile load of interest has caused a failure at the localized region.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute part of this specification. The drawings illustrate various features and embodiments of the invention, and together with the description serve to explain the principles and operation of the invention.

BRIEF DESCRIPTION OF THE DRAWINGS

The various advantages of the present invention will become apparent to one skilled in the art by reading the following specification and sub-joined claims and by referencing the following drawings, in which:

DETAILED DESCRIPTION OF THE PREFERRED EMBODIMENTS

Figure 1:
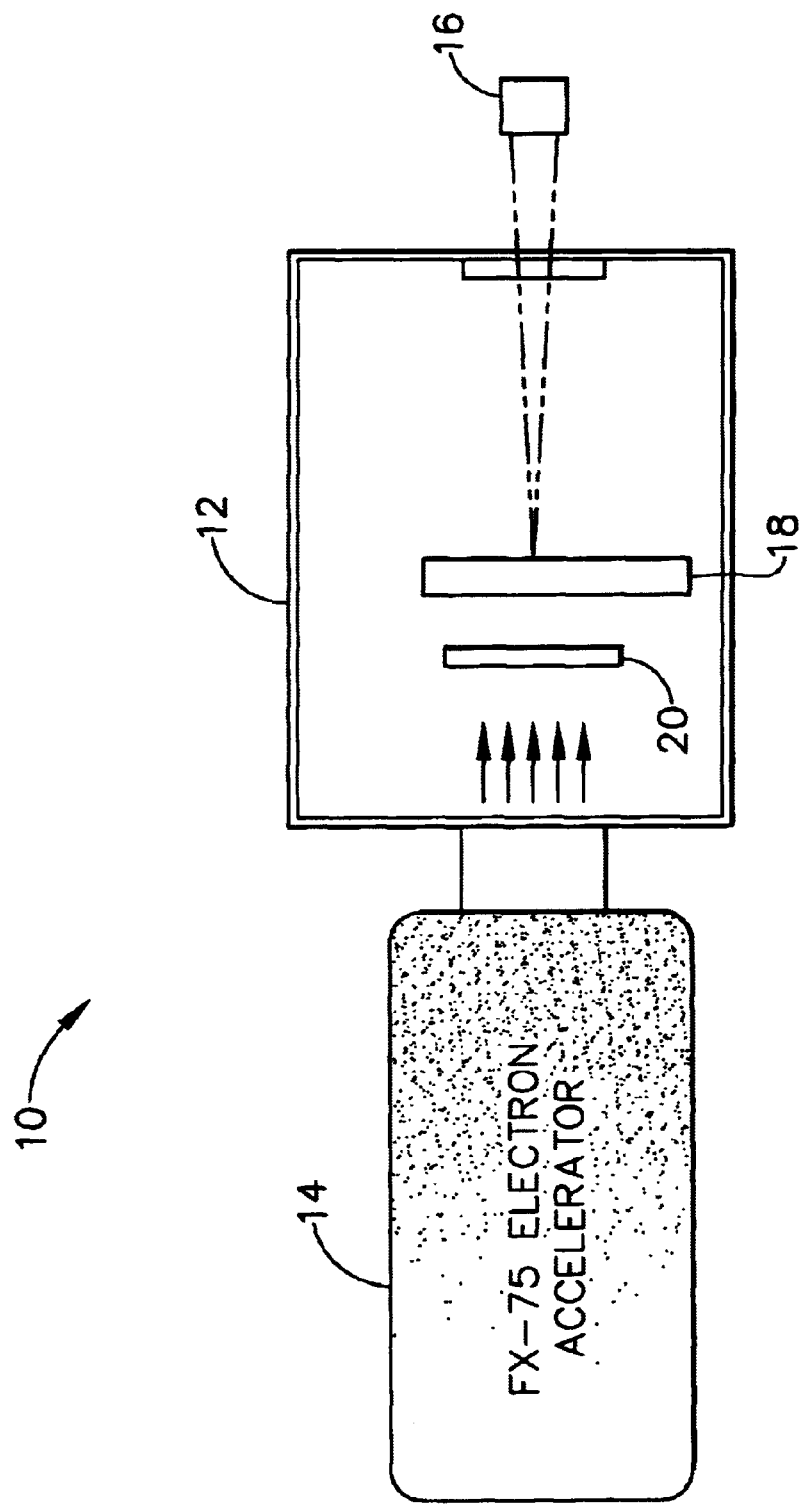
FIG. 1 is a side view a strength measurement system according to one embodiment of the invention.

Turning now to FIG. 1, the usefulness and functionality of the present invention can better be appreciated. It can be seen that a strength measurement system 10 generally includes a test chamber 12, an electron accelerator 14, and a surface measurement system 16. The test chamber 12 contains a test specimen 18, and the electron accelerator 14 applies electron beam irradiation to the test specimen 18. The electron beam irradiation bulk heats the test specimen 18 at a localized region such that the test specimen 18 is placed under a tensile load of interest. The mechanics of generating of the tensile of interest will be described in greater detail below. Nevertheless, the surface measurement system 16 determines whether the tensile load of interest has caused a failure at the localized region. Internal failures of composite materials are often referred to as spalling.

It is important to note that the above-described system 10 represents a marked improvement over conventional systems. For example, the measurement system 10 enables strength tests to be conducted on a much smaller scale. Thus, instead of designing a loading fixture large enough to test an entire aircraft wing when only a small portion of the wing is the actual target of the strength measurement, the measurement system 10 can test a localized region.

While the preferred embodiment will be described with respect to the testing of bonded composite materials, the invention is not so limited. In fact, the principles described herein can be applied to any test specimen that can be bulk heated without parting from the spirit and scope of the invention. Furthermore, while the preferred system places a specimen in a test chamber 12, it is envisioned that the electron beam can be brought out of the vacuum chamber through a window to allow the application of the strength testing to full scale structures. Furthermore, the optical measurement system can be located on the same side of the object under test as the bulk heating beam.

Theory of Operation

The electron beam irradiation is used to rapidly deposit energy in the test specimen 18. The rapid deposition heats the test specimen 18 faster than it can expand such that a compressional stress wave is generated in the specimen 18. When the stress wave reaches a free surface, it is reflected as a tension wave. The tension wave propagates back into the test specimen 18 such that a tensile load is generated. By adjusting the energy deposition from the electron beam irradiation, the test specimen 18 is subjected to a predescribed tensile load. Failure or survival of the test specimen 18 is determined by observing the motion of a free surface with the surface measurement system 16. It is highly preferred that the surface measurement system 16 includes a laser-based optical interferometer. A reflective layer may be added to the test specimen 18 to assist the optical interferometer, but such a layer is not required. Thus, strength testing under the present invention provides a type of proof testing where either a composition material or a joint between composition materials can be tested locally to a desired load level. If the specimen 18 does not fail, it can be used. If the specimen 18 fails, then it has insufficient strength for the application and should be rejected.

A calorimeter 20 is disposed between the electron accelerator 14 and the test specimen 18. The calorimeter 20 preferably includes a disk-shaped 0.05 millimeter thick titanium foil, with an attached thermocouple. The thermocouple measures the temperature rise in the titanium foil when the electron beam irradiation is fired. The energy dose (cal/gm) experienced by the calorimeter 20 is calculated from the temperature rise and the temperature dependent specific heat of the titanium. This calculation provides the energy dose immediately in front of the specimen 18. Thus, the calorimeter 20 enables calculation of a dosage level for the electron beam irradiation.

The dose absorbed in the composite may differ from that recorded by the calorimeter because of the differing stopping powers of titanium and the composite material. The absorbed dose, e, for a given material is $$e = F \Delta t S$$

where F is the electron flux ($cm^{-2}-s^{-1}$) over a time interval $\Delta t$ and S is the stopping power, whose units are $MeV\text{-}cm^2\text{-}gm^{-1}$. Therefore, for a given electron flux and shine time, $t_s$ ($\Delta t = t_s$), the absorbed dose is proportional to S. Hence, the dose absorbed in the composite, $e_c$, is related to that measured in the titanium calorimeter, $e_{Ti}$ by $$e_c = e_{Ti} S_c / S_{Ti}.$$

Figure 8:
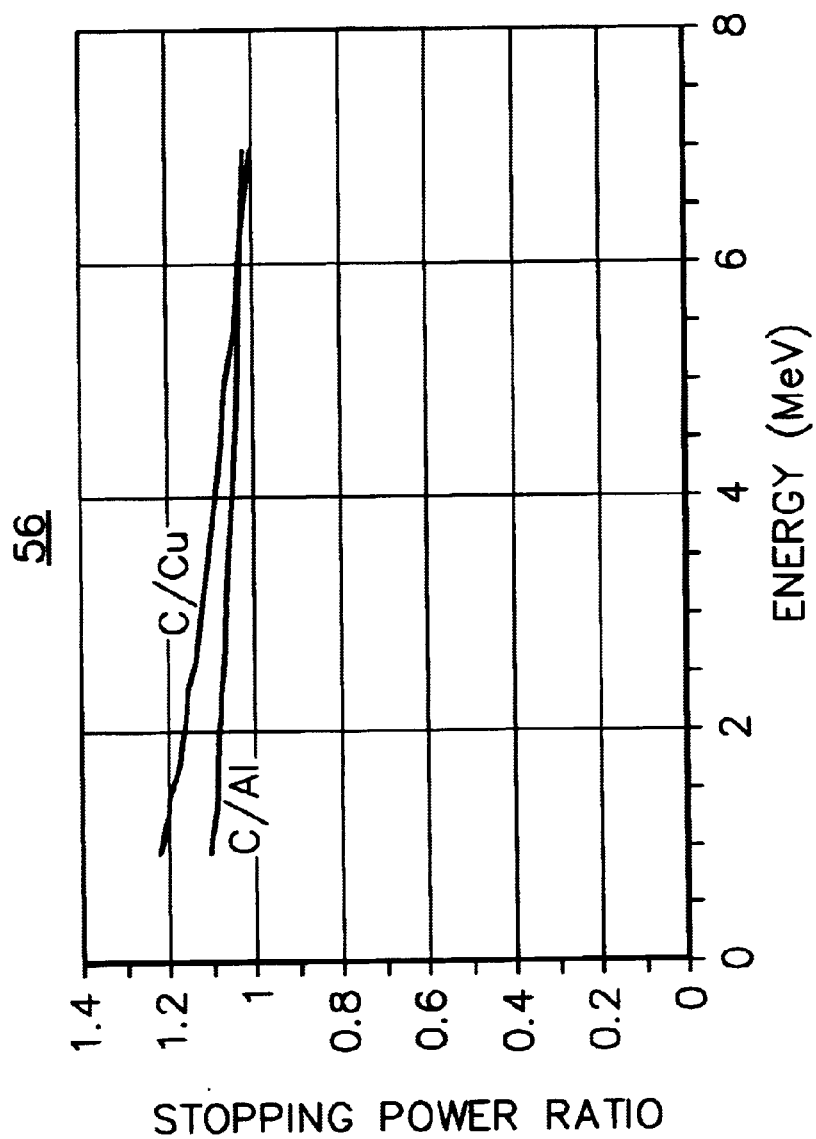
FIG. 8 is a plot showing stopping power ratios as a function of electron energy.

The article by Bichsel H. (1968) entitled "Charged-Particle Interactions", in *Radiation Dosimetry* (F. H. Attix, W. C. Roesche, E. Tochilin, eds.), Academic Press, New York, 157–228, provides a table of stopping power as a function of electron energy for various elements, including C (taken as representative of graphic composite), Al, and Cu. Although titanium is not listed specifically in the table, the values provided for Al (Z=13) and Cu (Z=29) conveniently bracket the Z value of Ti (Z=22). Therefore, the stopping power ratio, $S_c/S_{Ti}$, for graphic composite and TI should lie between the ratios for A/Al and C/Cu. FIG. 8 contains a plot 56 showing these ratios as a function of electron energy. For the typical range of energies used here (5 to 6 MeV), these data indicate that $S_c/S_{Ti}=1$, to within an error of only few percent. Therefore, the dose measured by the titanium calorimeter should closely approximate that absorbed in the near-surface region of the composite. It should be noted that, if future experiments are performed at significantly lower energies (e.g. 2 MeV), the difference in stopping powers becomes significant, and the dose in the composite may be 10–20% higher than that measured by the calorimeter 20.

The longitudinal wave speed is used indirectly in the calculation of stress, while the wave speed is determined from the velocity history measured at the rear surface of the specimen 18. The time interval between zero crossings in the velocity history is the time required for the shock to traverse the sample thickness, L. The first zero crossing is an exception, in that the e-beam shine time must be accounted for. Assume the beam turns on at time=0, and let $t_1, t_2, t_3, \ldots$ represent the first, second, (etc.) times when the velocity crosses through zero. The wave speed, $c_L$, is calculated from the first zero crossing as $$c_L = L/t_1 - t_s/2$$

where $t_s$ is the shine time (e.g., 70 ns). For subsequent zero crossings, the wave speed is calculated from $$c_L = L/(t_{i+1} - t_i) i > 0.$$

In the preferred approach, none of the specimens are instrumented with thermocouples, so temperature is not measured directly. Rather, specimen temperature is estimated from the dose and the specific heat. A handbook value for the specific heat of 0.3 cal/gm-C is adopted in the calculations.

For composite specimens thinner than a few millimeters, the absorbed dose does not vary significantly through the thickness of the specimen. In this case, the e-beam energy deposition initially produces a uniform compressive stress, σ, throughout the specimen of magnitude $$\sigma = \rho \Gamma e$$

where ρ is the density of the sample material, Γ is the Gruneisen coefficient and e is the dose. Reflection at the free surface generates a tensile stress of this same magnitude, up to the point that the dose is sufficiently high that yielding or fracture limits the stress. Therefore, the tensile stress generated by a given dose can be calculated if the Gruneisen coefficient is known.

Figure 9:
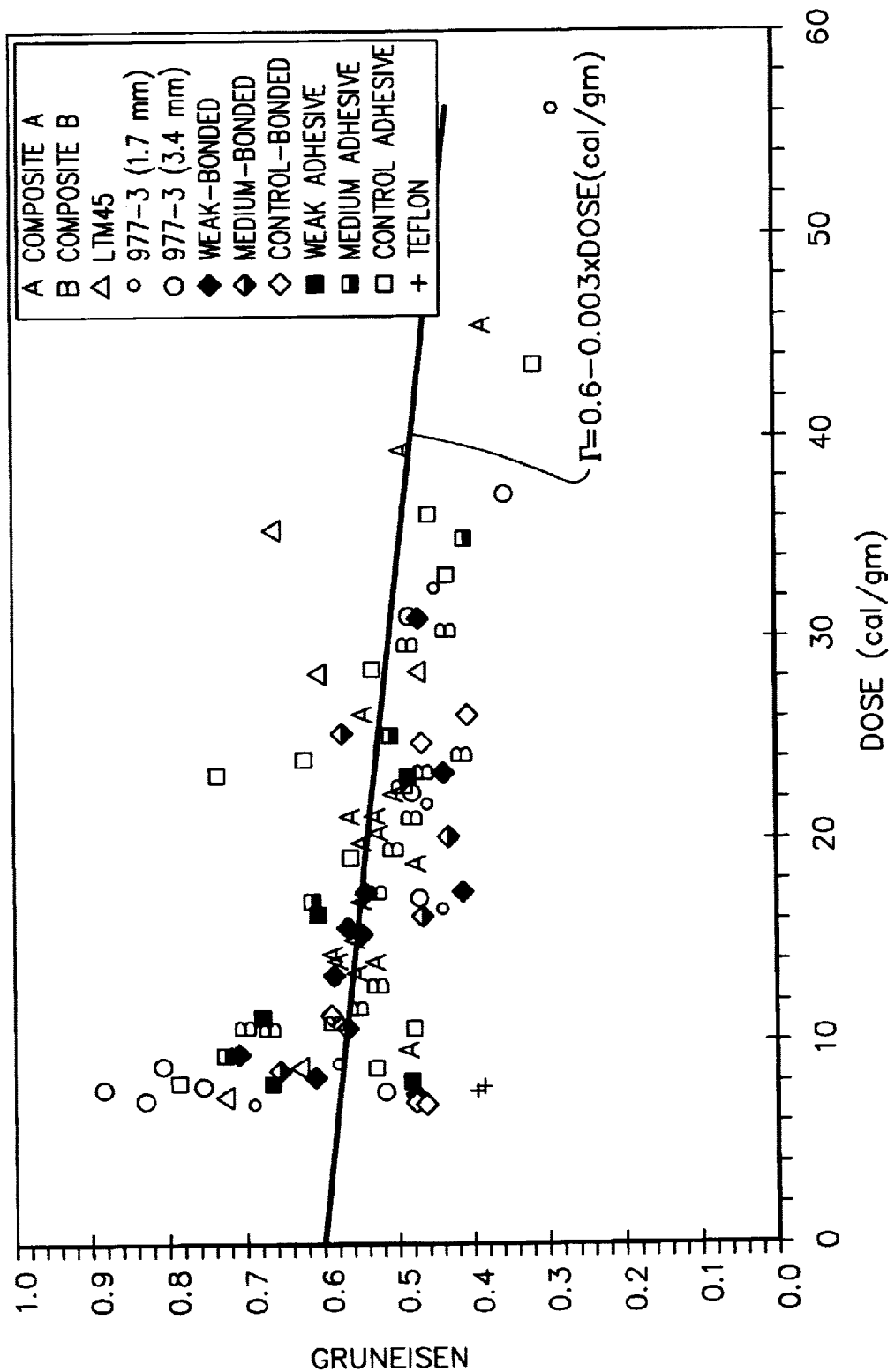
FIG. 9 is a plot showing the Gruneisen coefficient as a function of dose.

The Gruneisen coefficient is calculated from the well-known relation $$\Gamma = c_L v/e$$

where v is the peak velocity measured by the interferometer. FIG. 9 shows the values of Γ calculated from test results. Each point in the figure represents a single e-beam experiment, with the value of Γ calculated from the measured values of wave speed, peak surface velocity and dose. While there is considerable scatter in the data for a given specimen type, it is evident that Γ is only weakly dependent on dose (temperature). With the exception of the Teflon data, all of the composite and adhesive materials are fit reasonably well by the relation $$\Gamma = 0.6 - 0.003e$$

where e is expressed in cal/gm. The above relation is used to calculate stresses for the composite and adhesive specimens considered in this report. In the absence of sufficient data, Γ for Teflon is assumed to be 0.38, independent of dose.

Independent measurements of Γ are difficult to find in the literature. One source of relevant data is the report of Urzendowski R. and Guenter A. H. (1972) "Thermal Properties and Gruneisen Parameters for Several Polymers, Concretes, and Composite Materials", AFWL Tech. Rept. AFWL-TR-72-37. This article uses ultrasonic sound velocity data along with measurements of specific heat and linear coefficient of thermal expansion to calculate Γ for carbon phenolics. The reported values of Γ=0.46–0.52 at room temperature are comparable to the values measured under the present invention for composites. Additionally, the article notes only a slight decrease in Γ(~0.001/° C.) with increasing temperature.

Strength Measurement Procedure

Turning now to FIGS. 2–3, it will be appreciated that the preferred approach is to first probe the specimen with an energy dose well below that required for failure. This initial probe provides a baseline velocity (or displacement) waveform. The specimen is then subjected to an energy dose high enough to induce a tensile load of interest. Failure or survival of the bond is inferred from the measured free surface velocity history. The determination of failure of or survival can be confirmed by performing an additional low-dose probe test. If this test produces the same velocity history as measured in the first probe test, then the bond is known to have survived intact. Therefore, the strength of the bond is at least as large as the tensile load induced in the high-dose test.

This procedure can be used with progressively larger energy doses to determine the bond strength (i.e. test the bond to failure). Of course, the same procedure can be used for non-destructive verification of bond strength by performing the low-dose probe test, a second test at a dose necessary to certify the bond, and then the third probe test to ascertain failure or survival of the bond.

Thus, the high-dose test involves selecting a tensile load of interest for the test specimen and bulk-heating the test specimen at a localized region such that the test specimen is placed under the tensile load of interest. It is then determined whether the tensile load of interest has caused a failure at the localized region. As already noted, the preferred embodiment involves using bonded composite materials for the test specimen such that the localized test region is positioned at a bond between the composite materials.

As already discussed, normally when a material is heated, it expands. When the material is prevented from expanding during heating, the internal pressure increases. The present invention defines the heating time to be significantly less than the time for an acoustic wave to transit the test specimen such that the material of the test specimen is initially prevented from the expanding by its own inertia. The outer surfaces of the specimen must expand before the interior can expand, and this expansion is communicated at the local speed of sound in the material.

FIGS. 2A–2F illustrate that initially, the specimen is at a state of rest with zero stress σ, zero mid-plane particle velocity $U_{PMID}$, zero free surface particle velocity $U_{PFREE}$, and zero free surface displacement d. Since the preferred embodiment involves the electron beam depositing its energy in less than approximately 80 nanoseconds ($80 \times 10^{-9}$ seconds), the acoustic transit time through a nominally ¼ inch thick graphite composite is approximately 2 microseconds ($2 \times 10^{-6}$ seconds). Thus, the bulk of the material in the irradiated region is subjected to a sudden increase in internal hydrostatic pressure. The cross section of the part therefore rapidly transitions into State A illustrated in the state transition diagram 34. It is important to note that the $U_{PMID}$ plot 22 demonstrates that initially there is no change in particle velocity at the mid-plane. This is because the material is initially prevented from expanding by its own inertia. The free surfaces 24, 26, however, rapidly transition into States C and B, respectively. The $U_{PFREE}$ plot 28 therefore demonstrates a rapid increase in particle velocity at the free surfaces 24, 26. It can also be seen that the d plot 30 demonstrates a gradual increase in free surface displacement. The σ plot 32 illustrates that the mid-plane of the specimen is under compression (i.e., positive σ) while the mid-plane is in State A. It is important to note that this hydrostatic pressure does not cause the material to fail, since there is no strain associated with it.

The potential for failure arises when the stress waves resulting from the expansion of the free surfaces 24, 26 propagate and produce strain. This is analogous to two locomotives pulling on opposite ends of a train where all of the couplers are initially compressed. The wave speed (the rate at which the taking up of the slack moves from car to car) is much faster than the particle velocity (the speed of the individual cars). The maximum tensile stress occurs when the two waves cross each other.

Figure 2A:
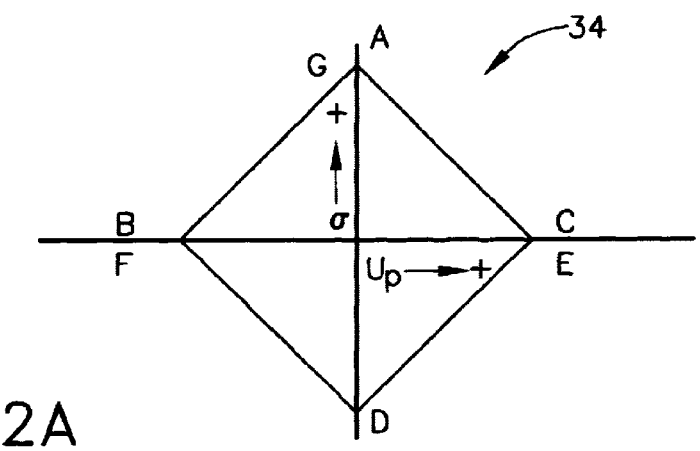
FIG. 2A is a state transition diagram for a strength test wherein no failure occurs.
Figure 2B:
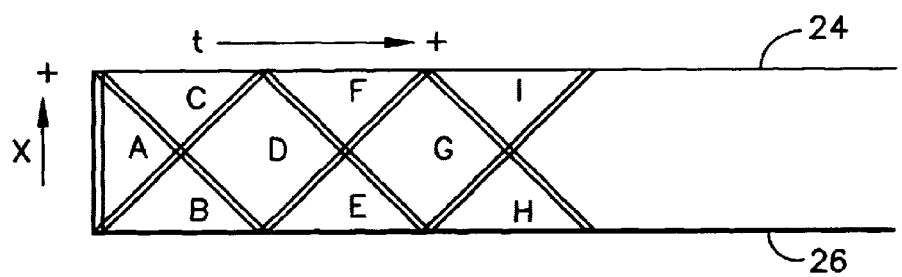
FIG. 2B is a plot of the position of the stress waves in a specimen over time where no failure occurs during strength testing. The double lines indicate the shine time of the bulk heating pulse.
Figure 2C:
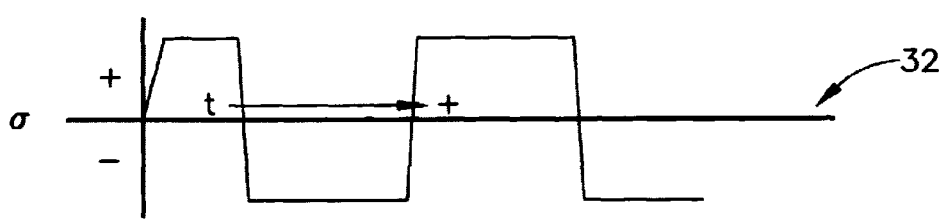
FIG. 2C is a plot showing mid-plane stress over time wherein no failure occurs during strength testing.
Figure 2D:
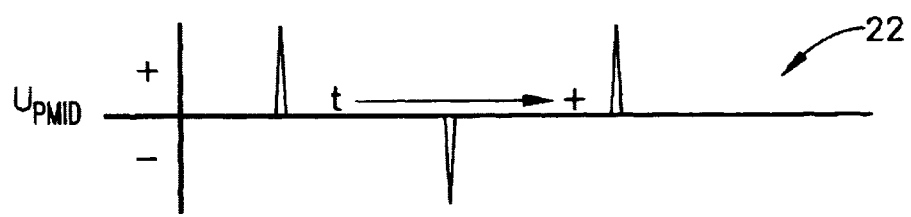
FIG. 2D is a plot showing mid-plane particle velocity over time wherein no failure occurs during strength testing.
Figure 2E:
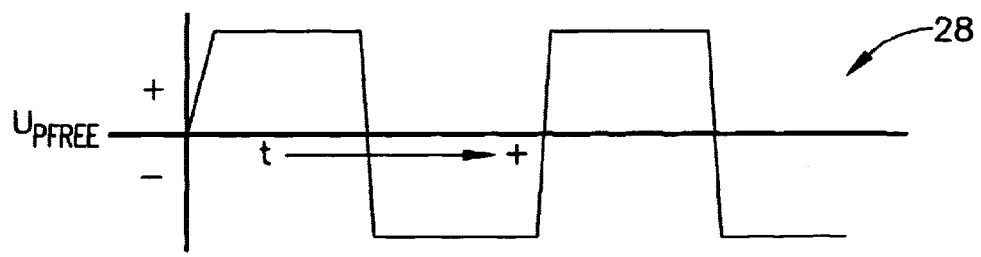
FIG. 2E is a plot showing free surface particle velocity over time wherein no failure occurs during strength testing.
Figure 2F:
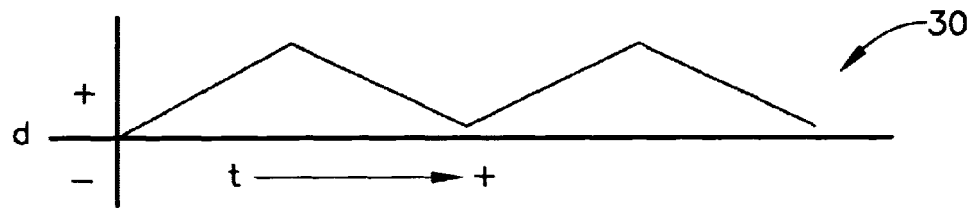
FIG. 2F is plot showing free surface displacement over time wherein no failure occurs during strength testing.
Figure 3A:
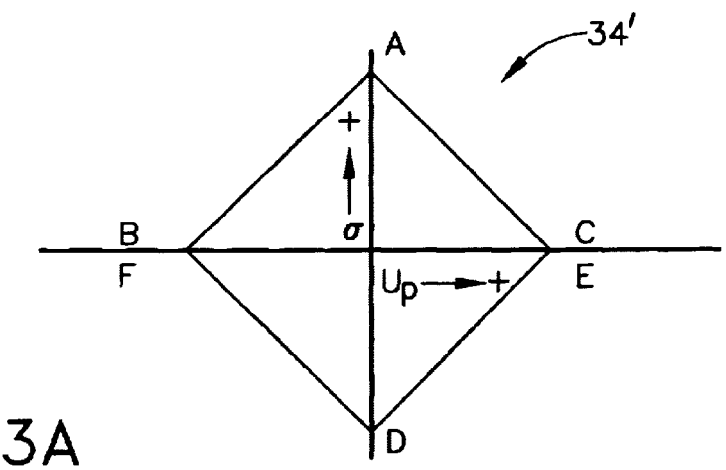
FIG. 3A is a state transition diagram for a strength test wherein mid-plane spall occurs.
Figure 3B:
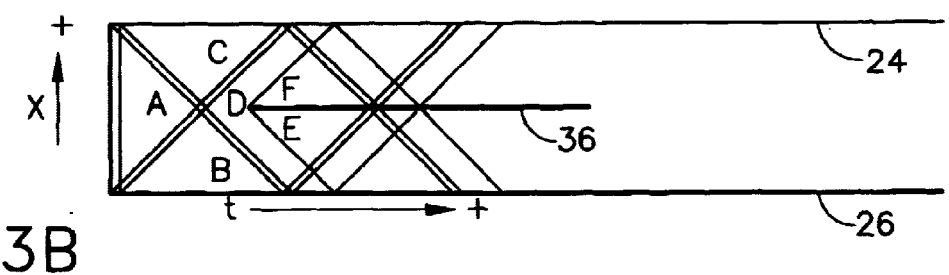
FIG. 3B is a plot of the position of the stress waves in specimen over time wherein midplane spall occurs during strength testing.
Figure 3C:
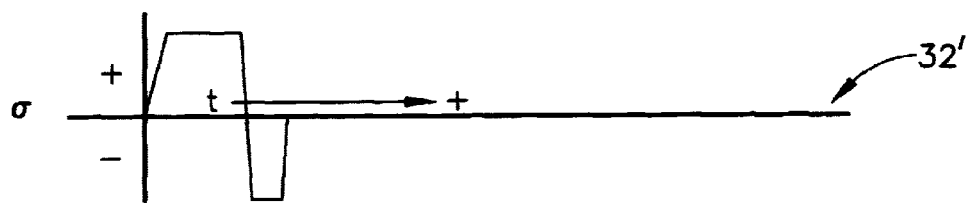
FIG. 3C is a plot showing mid-plane stress over time wherein mid-plane spall occurs during strength testing.
Figure 3D:
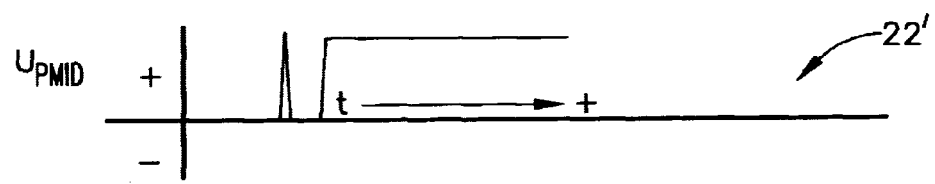
FIG. 3D is a plot showing mid-plane particle velocity over time wherein mid-plane spall occurs during strength testing.
Figure 3E:
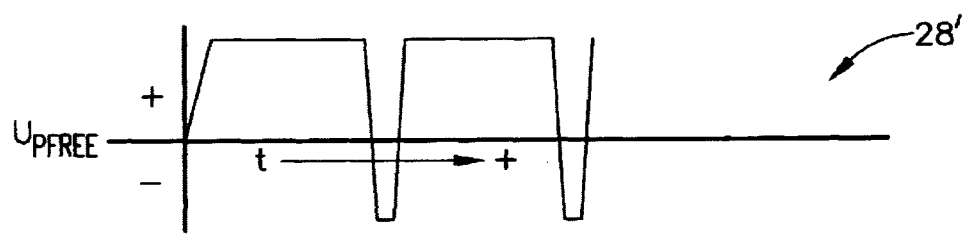
FIG. 3E is a plot showing free surface particle velocity over time wherein mid-plane spall occurs during strength testing.
Figure 3F:
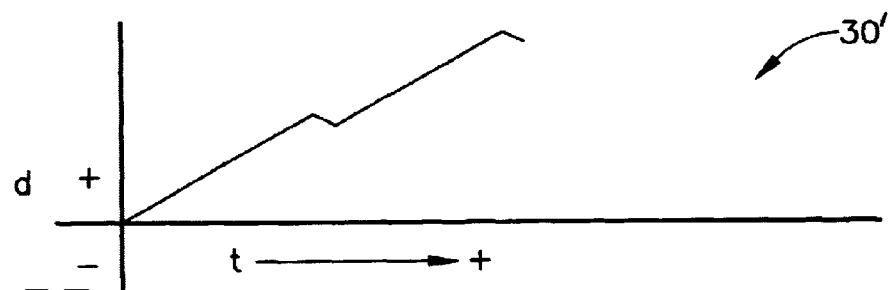
FIG. 3F is a plot showing free surface displacement over time wherein mid-plane spall occurs during strength testing.

Thus, when the mid-plane reaches State D the specimen is placed under tensile load. Thus, σ goes negative as illustrated in plot 32. It is important to note that the surface measurement system is able to monitor the $U_{PFREE}$ plot 28 and the d plot 30. Since FIG. 2 represents the scenario of the strength of the material being stronger than the maximum negative value of σ (and therefore no failure or spalling occurs) plots 28 and 30 provide valuable information. For example, when the free surfaces 24, 26 transition to States F and E, respectively, the $U_{PFREE}$ plot 28 demonstrates a change in particle velocity from a positive value to a negative value. Thus, the surfaces change direction as illustrated in plot 30. If no mid-plane spall occurs, the free surfaces 24, 26 will continue moving inward as illustrated in FIGS. 2E and 2F.

As best illustrated in FIG. 3, however, if spall occurs the specimen will behave differently. Thus, it can be seen that while state transition diagram 34' generally indicates the same transitions, the $U_{PFREE}$ plot 28' and d plot 30' are quite different. For example, it can be seen that as the free surfaces 24, 26 leave State D and the particle velocity transitions from a positive value to a negative value, a failure has already occurred at the mid-plane 36. Since the failure causes the mid-plane particle velocity to go positive as indicated in plot $U_{PMID}$ plot 22', the free surfaces 24, 26 can move inwardly by only a certain amount. When the free surface particles collide with the mid-plane particles, it can be seen that both the $U_{PFREE}$ plot 28' and the d plot 30' demonstrate that the free surfaces 24, 26 are pushed outwardly by the internal particles.

Thus, by controlling the dose of the irradiation source, the peak tensile stress can be controlled. If this peak tensile stress exceeds the local strength of the material, the sample will fail and the results of this failure will be detected in the surface measurement records.

Figure 4:
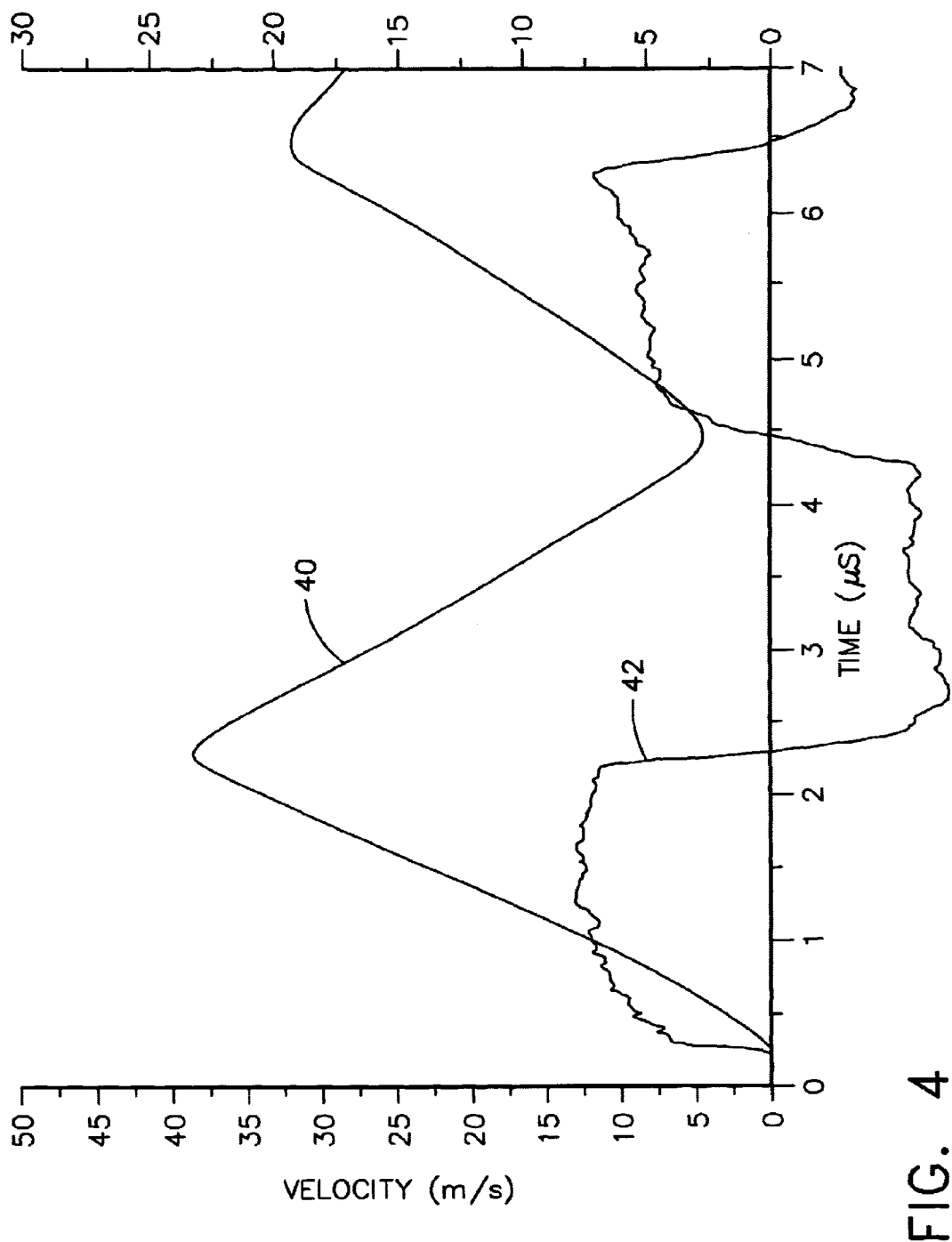
FIG. 4 is an interferometer plot showing free surface displacement and free surface velocity wherein no failure occurs during strength testing.

Turning now to FIG. 4, it can further be seen that the present invention provides a method for determining whether the tensile load of interest has caused a failure at the localized region of the test specimen. Generally, the method includes the step of observing a free surface of the test specimen with a surface measurement system such as an optical interferometer. A measurement response of the free surface is determined with the optical interferometer, where the measurement response results from the tensile load of interest. The method further provides for determining whether the measurement response corresponds to a failure of the test specimen. FIG. 4 therefore illustrates a surface velocity curve 40 and a surface displacement curve 42. As discussed above, the curves 40, 42 result from bulk heating the test specimen such that the test specimen is placed under an intermediate tensile load. The intermediate tensile load is lower than the tensile load of interest such that the intermediate tensile load does not cause a failure at the localized region. A calibration response of the free surface is therefore determined with the optical interferometer, where the calibration response results from the intermediate tensile load and is defined by curves 40, 42.

Figure 5:
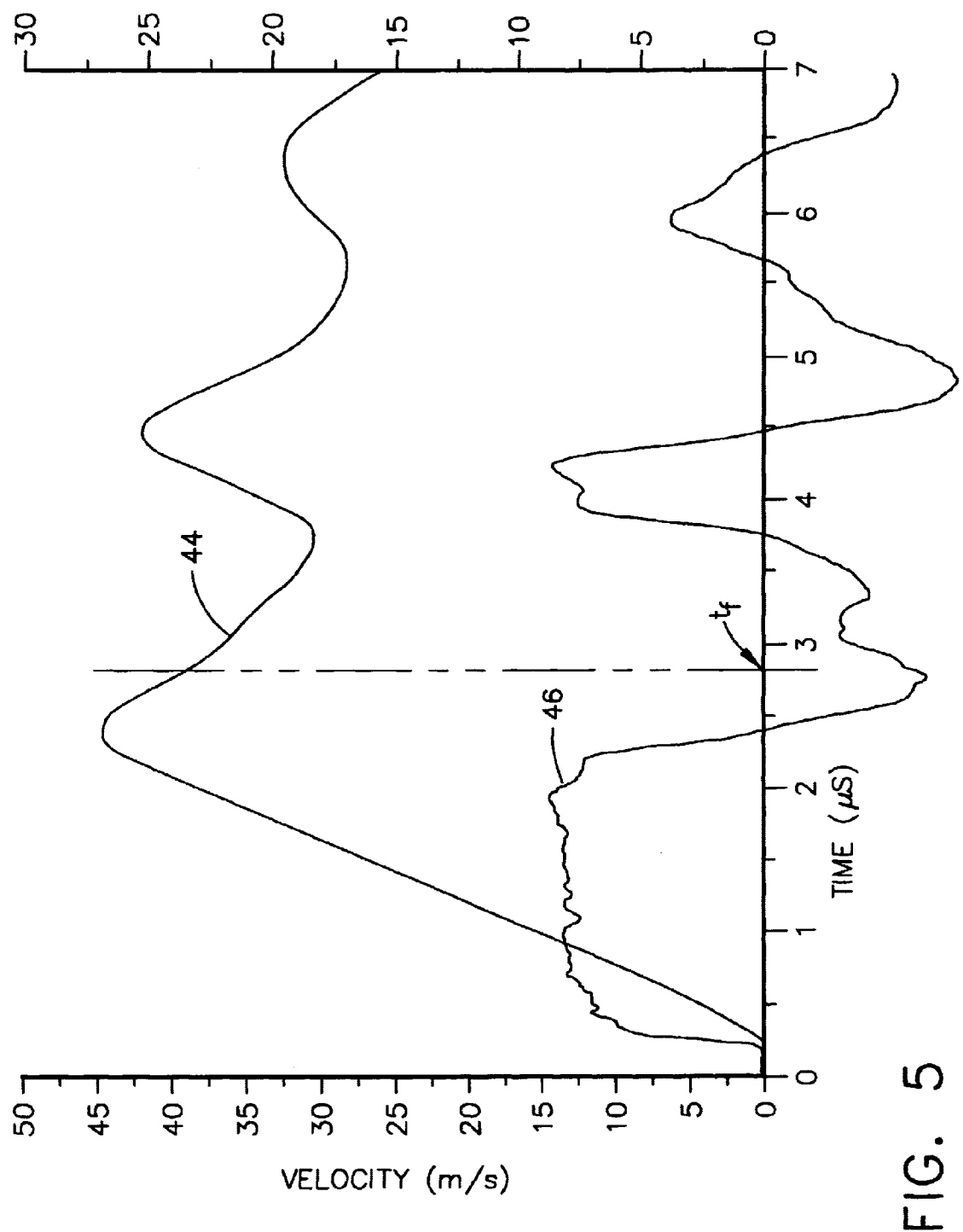
FIG. 5 is an interferometer plot showing free surface displacement and free surface velocity wherein a failure occurs during strength testing.

FIG. 5 demonstrates the usefulness of comparing the measurement response with the calibration response. It can be seen here that the surface velocity curve 44 and the surface displacement curve 46 demonstrate a failure of the specimen at the localized region. For example, at time $t_f$ the shapes of both curves 44 and 46 change with respect to the shapes of curves 40 and 42 of FIG. 4.

Figure 6:
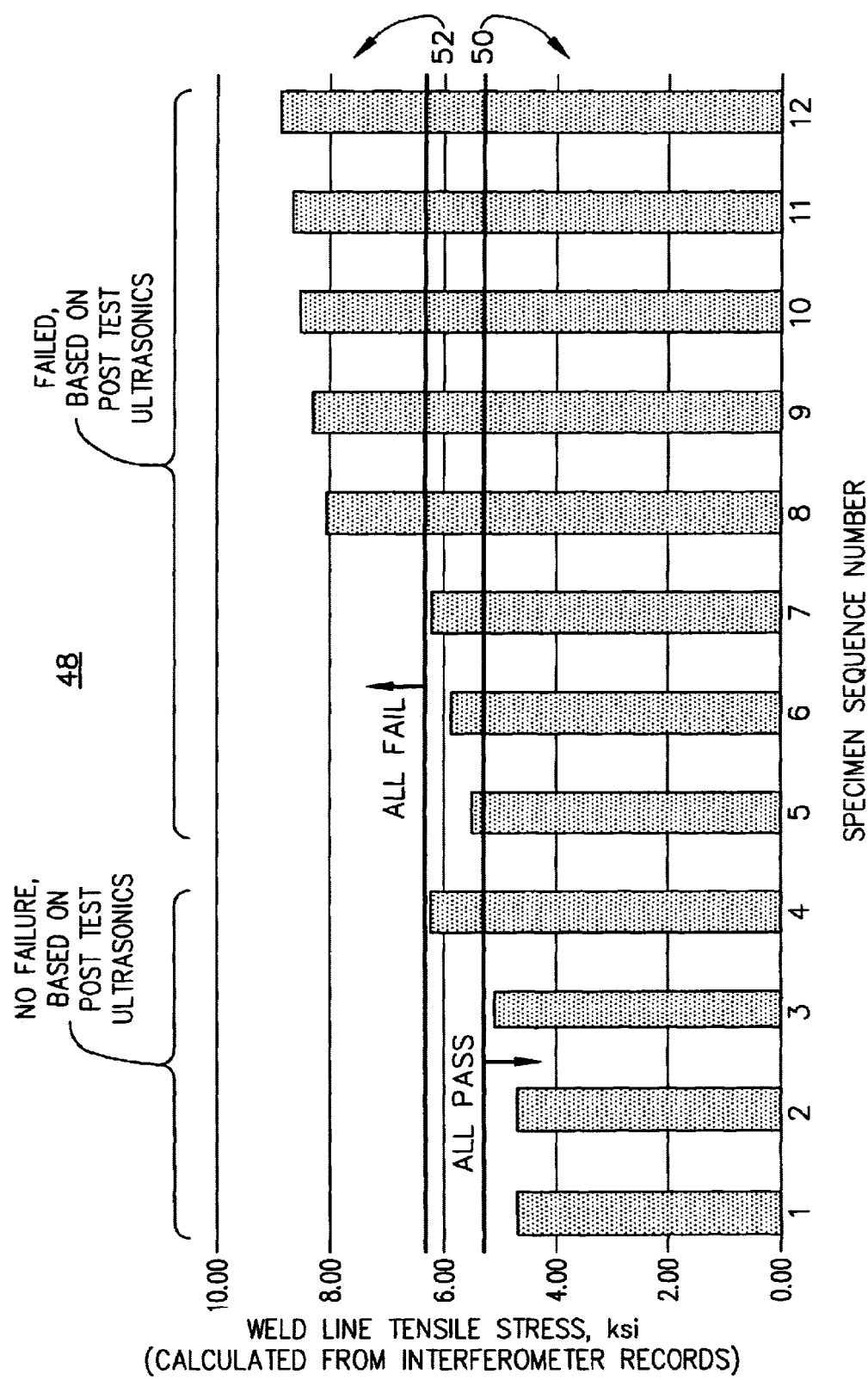
FIG. 6 is a chart correlating stress measured using an interferometer wherein failures are confirmed with ultrasonics.

FIG. 6 demonstrates the effectiveness of the present invention at chart 48. Generally, FIG. 6 shows the correlation between internal stress and failure of the local region. Specifically, it can be seen that a pass region 50 and a fail region 52 can be defined for the test specimens. It can further be seen that the majority of the test specimens fall into one of these regions. Test results were confirmed using a 5 MHz transmission ultrasonic scan. Lack of ultrasonic transmission can be used as an indicator of internal damage.

Figure 7:
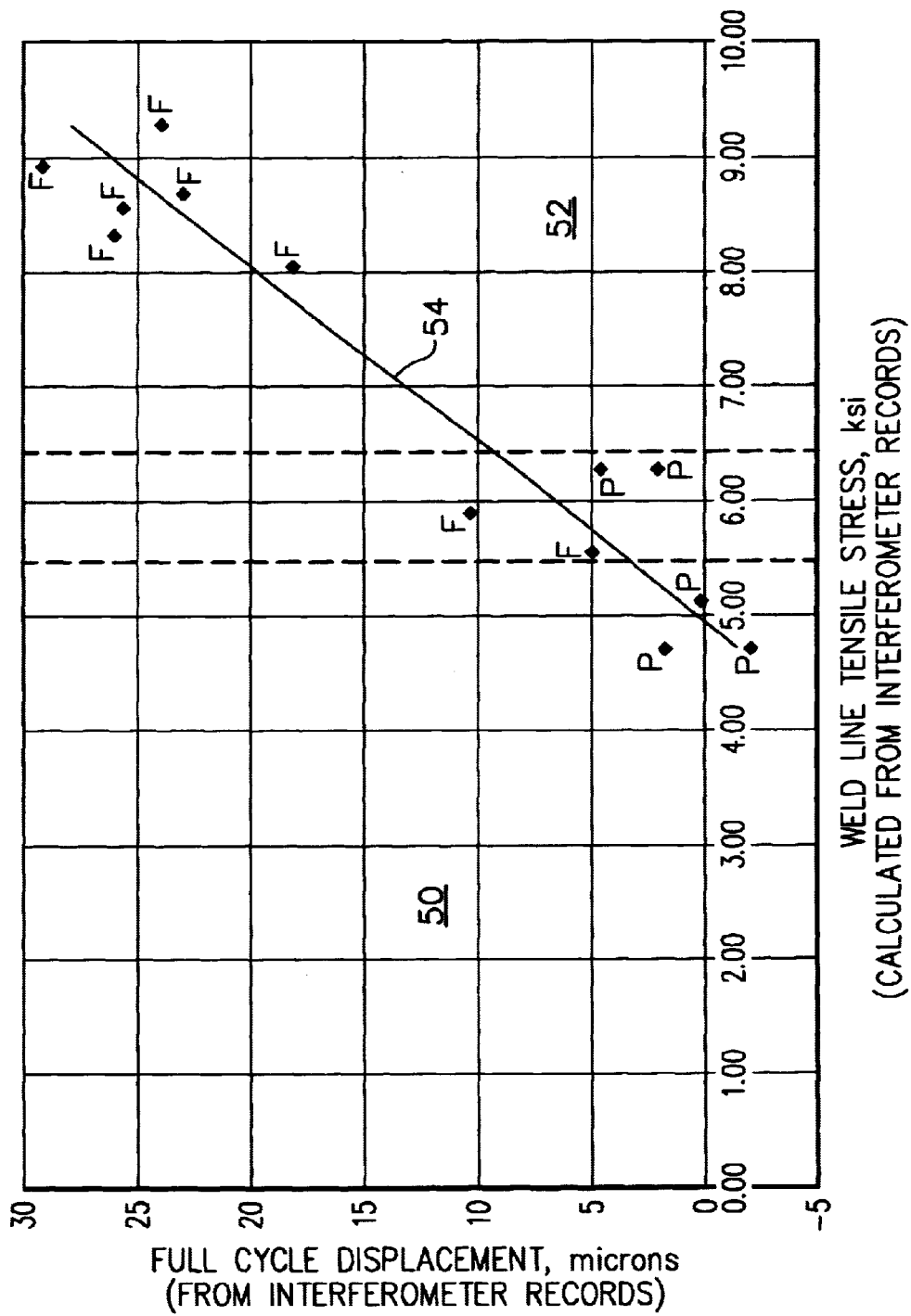
FIG. 7 is a plot showing displacement vs. joint stress.

FIG. 7 includes a plot 54 showing the correlation between net displacement of a free surface (a critical feature of the response) and failure of the local region. Once again, a pass region 50 and a fail region 52 can be readily defined for the test specimens.

Those skilled in the art can now appreciate from the foregoing description that the broad teachings of the present invention can be implemented in a variety of forms. Therefore, while this invention can be described in connection with particular examples thereof, the true scope of the invention should be not so limited since other modifications will become apparent to the skilled practitioner upon a study of the drawings, specification and following claims.

What is claimed:

1. A method for measuring a strength of a test specimen, the method comprising the steps of:

selecting a tensile load of interest for the test specimen;

bulk heating the test specimen at a localized region such that the test specimen is placed under the tensile load of interest;

using composite materials for the test specimen such that the localized region is positioned at an interface between the composite materials;

determining a measurement response resulting from the tensile load of interest;

bulk heating the test specimen such that the test specimen is placed under an intermediate tensile load, the intermediate tensile load being lower than the tensile load of interest such that the intermediate tensile load does not cause a failure at the localized region;

determining a calibration response resulting from the intermediate tensile load; and comparing the measurement response to the calibration response.

2. The method of claim 1 further including the steps of:

observing a free surface of the test specimen with an optical interferometer;

determining a measurement response of the free surface with the optical interferometer, the measurement response resulting from the tensile load of interest; and determining whether the measurement response corresponds to a failure of the test specimen.

3. The method of claim 2 further including the steps of:

bulk heating the test specimen such that the test specimen is placed under an intermediate tensile load, the intermediate tensile load being lower than the tensile load of interest such that the intermediate tensile load does not cause a failure at the localized region;

determining a calibration response of the free surface with the optical interferometer, the calibration response resulting from the intermediate tensile load; and comparing the measurement response to the calibration response.

4. The method of claim 1 further including the step of selecting surface displacement as the calibration response.

5. The method of claim 1 further including the step of selecting surface velocity as the calibration response.

6. The method of claim 2 further including the step of selecting surface displacement as the measurement response.

7. The method of claim 2 further including the step of selecting surface velocity as the measurement response.

8. The method of claim 1 further including the steps of:
calculating a measurement dosage level, the measurement dosage level corresponding to the tensile load of interest; and
applying electron beam irradiation to the test specimen, the electron beam irradiation having the measurement dosage level such that the electron beam irradiation generates the tensile load of interest.

9. The method of claim 8 further including the step of increasing the electron beam irradiation until the test specimen fails at the localized region.

10. The method of claim 1 further including the step of using bonded composite materials for the test specimen such that the interface comprises a bond between the composite materials.

11. The method of claim 10 further including the step of using parts of an aircraft structure for the composite materials.

12. A method for determining whether a tensile load of interest has caused a failure at a localized region of a test specimen, the method comprising the steps of:
observing a free surface of the test specimen with an optical interferometer;
determining a measurement response of the free surface with the optical interferometer, the measurement response resulting from the tensile load of interest;
determining whether the measurement response corresponds to a failure of the test specimen;
bulk heating the test specimen at the localized region such that the test specimen is placed under an intermediate tensile load, the intermediate tensile load being lower than the tensile load of interest such that the intermediate tensile load does not cause a failure at the localized region;
using composite materials for the test specimen such that the localized region is positioned at an interface between composite materials;
determining a calibration response of the free surface with the optical interferometer, the calibration response resulting from the intermediate tensile load; and
comparing the measurement response to the calibration response.

13. The method of claim 12 further including the step of selecting surface displacement as the calibration response.

14. The method of claim 12 further including the step of selecting surface velocity as the calibration response.

15. The method of claim 12 further including the step of selecting surface displacement as the measurement response.

16. The method of claim 12 further including the step of selecting surface velocity as the measurement response.

17. A strength measurement system comprising:
a test cell containing a test specimen;
an electron accelerator for applying electron beam irradiation to the test specimen, the electron beam irradiation bulk heating the test specimen at a first localized region such that the test specimen is placed under a tensile load of interest and a second localized region such that the test specimen is placed under an intermediate tensile load,
wherein composite materials are used for the test specimen such that the localized region is positioned at an interface between the composite materials;
a surface measurement system for determining whether the tensile load of interest has caused a failure at the localized region, and determining a calibration response resulting from the intermediate tensile load.

18. The strength measurement system of claim 17 wherein the surface measurement system includes an optical interferometer.

19. The strength measurement system of claim 17 further including a calorimeter disposed between the electron accelerator and the test specimen such that the calorimeter enables calculation of a dosage level for the electron beam irradiation.

* * * * *